United States Patent [19]

Seebach

[11] Patent Number: 4,703,033

[45] Date of Patent: Oct. 27, 1987

[54] NOVEL CYCLOSPORINS

[75] Inventor: Dieter Seebach, Zurich, Switzerland

[73] Assignee: Sandoz Ltd., Basel, Switzerland

[21] Appl. No.: 837,434

[22] Filed: Mar. 7, 1986

[30] Foreign Application Priority Data

Mar. 11, 1985 [GB] United Kingdom ............... 8506230
May 1, 1985 [GB] United Kingdom ............... 8511029
Jan. 31, 1986 [GB] United Kingdom ............... 8602370

[51] Int. Cl.$^4$ .................... A61K 37/02; C07K 5/12
[52] U.S. Cl. ............................... 514/11; 530/317; 530/321
[58] Field of Search ............... 514/11; 530/317, 321

[56] References Cited

PUBLICATIONS

Chem. Abstr. vol. 105 (1986) 218544.
Chem. Abstr. vol. 100, (1984) 132001.
Chem. Abstr. vol. 105, (1986) 164395.

*Primary Examiner*—Delbert K. Phillips
*Attorney, Agent, or Firm*—Gerald D. Sharkin; Robert S. Honor; Thomas O. McGovern

[57] ABSTRACT

Cyclosporins e.g. of formula II $$\begin{array}{l} \text{—X-Y-Z-MeLeu-Val-MeLeu-Ala-(D)Ala-MeLeu-MeLeu-MeVal—} \\ \phantom{—}1\ 2\ 3\ \phantom{..}4\ \phantom{....}5\ \phantom{......}6\ \phantom{......}7\ \phantom{....}8\ \phantom{......}9\ \phantom{.....}10\ \phantom{.....}11 \end{array} \quad (\text{II})$$

in which
X is -MeBmt- or -dihydro-MeBmt- and
Y is -αAbu-, -Thr-, -Val- or -Nva-, wherein the residue at the 3-position, i.e. the residue Z in formula II, is an optically active, α-N-methylated α-amino acid residue of the (D)-configuration, possess pharmaceutical, in particular immunosuppressive, anti-inflammatory and anti-parasitic activity. Intermediate cyclosporin poly-anions having a de-protonated sarcosyl residue at the 3-position, e.g. polyanions of cyclosporins of formula II above wherein X and Y have the meanings given above and Z is -Sar-, in which the said residue Z is de-protonated, are also novel and part of the invention.

17 Claims, No Drawings

NOVEL CYCLOSPORINS

The present invention relates to novel cyclosporins, their use as pharmaceuticals and pharmaceutical compositions comprising them, as well as to processes for the production of said novel cyclosporins and novel intermediates.

The cyclosporins comprise a class of structurally distinctive, cyclic, poly-N-methylated undecapeptides commonly possessing pharmacological, in particular immunosuppressive, anti-inflammatory and anti-parasitic activity. The first of the cyclosporins to be isolated and the "parent" compound of the class, is the naturally occurring fungal metabolite Cyclosporine, also known as cyclosporin A, of formula A

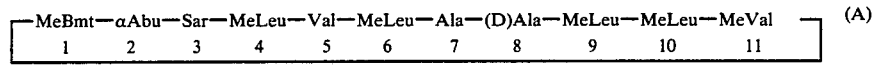 (A)

wherein -MeBmt- represents the N-methyl-(4R)-4-but-2E-en-1-yl-4-methyl-(L)threonyl residue of formula B

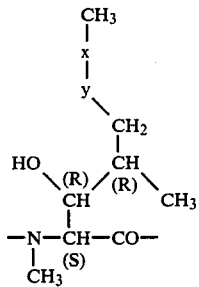 (B)

in which -x-y- is —CH=CH—(trans).

Since the original discovery of Cyclosporine a wide variety of naturally occurring cyclosporins has been isolated and identified and many further non-natural cyclosporins have been prepared by total- or semi-synthetic means or by the application of modified culture techniques. The class comprised by the cyclosporins is thus now substantial and includes for example the naturally occurring cyclosporins A through Z [c.f. Kobel et al. European Journal of applied Microbiology and Biotechnology 14, 237-240 (1982) and poster presented by Traber et al., 24th. Interscience Conference on Antimicrobial Agents and Chemotherapy, Washington, October 8-10, (1984)]; as well as various non-natural or artificial cyclosporins, including dihydro-cyclosporins (in which the group -x-y- of the -MeBmt- residue—see formula B above—is saturated, e.g. as disclosed in U.S. Pat. Nos. 4,108,985; 4,210,581 and 4,220,641), cyclosporins in which the -MeBmt- residue is present in isomeric or N-desmethyl form [c.f. European Pat. No. 0 034 567 and "Cyclosporin A", Proc. Internat. Conference on Cyclosporin A, Cambridge (U.K.) September 1981, Ed. D. J. G. White, Elsevier Press (1982)—both describing the total-synthetic method for the production of cyclosporins developed by R. Wenger] and cyclosporins in which incorporation of variant amino acids at specific positions within the peptide sequence is effected (c.f. European Pat. No. 0 056 782). Examples of such cyclosporins as disclosed in the above art references include e.g. [Thr]$^2$—, [Val]$^2$— and [Nva]$^2$-Cyclosporine (also known as cyclosporins C, D and G respectively), [Dihydro-MeBmt]$^1$-[Val]$^2$-Cyclosporine (also known as dihydrocyclosporin D) and [(D)Ser]$^8$- and [Dihydro-MeBmt]$^1$-[(D)Ser]$^8$-Cyclosporine.

[In accordance with now conventional nomenclature for the cyclosporins, these are defined herein by reference to the structure of Cyclosporine (i.e. cyclosporin A). This is done by first indicating those residues in the molecule which differ from those present in Cyclosporine and then applying the term "Cyclosporine" to characterise the remaining residues which are identical to those present in Cyclosporine. At the same time the term -dihydro-MeBmt- is employed to designate the residue of formula B above in which -x-y- is —CH$_2$—CH$_2$—. Thus [Dihydro-MeBmt]$^1$-Cyclosporine is the cyclosporin having the sequence shown in formula A, but in which -MeBmt- [formula B, -x-y-=—CH=CH—(trans)] at the 1-position is replaced by -dihydro-MeBmt- [formula B, -x-y-=—CH$_2$—CH$_2$—]. Similarly [Val]$^2$-Cyclosporine is the cyclosporin having the sequence shown in formula A, but in which -αAbu- at the 2-position is replaced by -Val-.

In addition, amino acid residues referred to by abbreviation, e.g. -Ala-, -Meval- etc . . . are, in accordance with conventional practice, to be understood as having the (L)-configuration unless otherwise indicated. Residue abbreviations preceded by "Me", as in the case of -MeLeu-, represent N-methylated residues. The individual residues of the cyclosporin molecule are numbered, as in the art, clockwise and starting with the residue -MeBmt- or -dihydro-MeBmt- in position 1. The same numerical sequence is employed throughout the present specification and claims.]

Characteristic of cyclosporins hitherto described in the art has been the presence of a sarcosyl residue at the 3-position, providing the sole, non-optically active residue of the basic cyclosporin peptide sequence. The preparation of [(D)Pro]$^3$-Cyclosporine by total synthesis has been described. (see e.g. Sandorama 1984/III, p.p. 5-11). However, although this compound, in which the 3-sarcosyl residue is replaced by the cyclic (D)prolyl residue, is assumed to possess an almost identical configuration to Cyclosporine itself, it is reported as substantially lacking in immunosuppressive activity.

The present invention provides, inter al., an entirely novel method permitting direct derivatisation of the α-carbon atom of the sarcosyl residue commonly present at the 3-position of the cyclosporin molecule. Product cyclosporins obtained have an optically active, α-N-methylated amino acid residue of the (d)-configuration of the 3-position and thus comprise a distinct and wholly novel group. Moreover, although, as in the case of [(D)Pro]$^3$-Cyclosporine, a further optically active centre is introduced into the basic cyclosporine molecule, such cyclosporins have been found to possess useful pharmaceutical, e.g. immunosuppressive, anti-inflammatory or anti-parasitic activity.

In accordance with the foregoing the present invention provides, in a first aspect, a cyclosporin having an optically active, α-N-methylated α-amino acid residue at the 3-position, said residue having the (D)-configuration.

Preferred cyclosporins in accordance with the present invention are those wherein the amino acid residue at the 3-position has the formula I

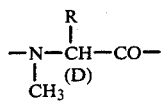

wherein r is:

(i) $C_{1-6}$alkyl or halo-substituted $C_{1-6}$alkyl; (ii) hydroxy-($C_{1-6}$-alkyl); (iii) thio-($C_{1-6}$alkyl); (iv) amino-($C_{1-6}$alkyl); (v) ($C_{2-5}$-alkoxycarbonylamino)-($C_{1-4}$alkyl); (vi) nitro-($C_{1-6}$alkyl) or cyano-($C_{1-5}$alkyl); (vii) ($C_{1-6}$alkoxy)-($C_{1-6}$alkyl) or ($C_{1-6}$alkylthio)-($C_{1-6}$alkyl); (viii) ($C_{2-7}$alkanoyloxy)-($C_{1-6}$alkyl); (ix) ($C_{2-7}$diazoalkanoyloxy)-($C_{1-6}$alkyl); (x) carboxy-($C_{1-6}$alkyl) or ($C_{2-7}$alkoxycarbonyl)-($C_{1-6}$alkyl); (xi) aminocarbonyl-($C_{1-4}$alkyl); (xii) aminoaminocarbonyloxy-($C_{1-4}$alkyl) or amino-($C_{2-9}$alkanoyloxy)-($C_{1-4}$alkyl); (xiii) amino-($C_{2-9}$alkoxycarbonyl)-($C_{1-4}$alkyl); (xiv) $C_{2-7}$alkylcarbonyl; (xv) $C_{2-7}$alkoxycarbonyl; (xvi) $C_{1-6}$alkylthio or hydroxy-($C_{1-6}$alkylthio); (xvii) ($C_{1-6}$alkoxy)-($C_{1-6}$alkylthio); (xviii) ($C_{2-11}$alkanoyloxy)-($C_{2-4}$alkylthio); (xix) ($C_{2-11}$alkanoyloxy)-($C_{2-4}$alkylsulfinyl) or -($C_{2-4}$alkylsulfonyl); (xx) aminocarbonyloxy-($C_{2-4}$alkylthio) or ($C_{2-11}$aminoalkanoyloxy)-($C_{2-4}$alkylthio); (xxi) aminocarbonyloxy-($C_{2-4}$alkylsulfinyl) or -($C_{2-4}$alkylsulfonyl), or ($C_{2-11}$aminoalkanoyloxy)-($C_{2-4}$alkyl-sulfinyl) or -($C_{2-4}$alkylsulfonyl); (xxii) aminocarbonyl; (xxiii) $C_{3-6}$alkenyl, $C_{3-6}$alkinyl, or halo-substituted $C_{3-6}$alkenyl or $C_{3-6}$alkinyl; (xxiv) hydroxy-($C_{3-6}$alkenyl); (xxv) aryl-($C_{1-6}$alkyl) or hydroxy-substituted aryl-($C_{1-6}$alkyl); (xxvi) aryl-($C_{3-6}$-alkenyl), aryl-($C_{3-6}$alkinyl), or hydroxy-substituted aryl-($C_{3-6}$-alkenyl) or aryl-($C_{3-6}$alkinyl); (xxvii) arylthio; (xxviii) heteroarylthio; (xxix) aryl-($C_{2-5}$alkoxycarbonylamino)-($C_{1-4}$alkyl); (xxx) halogen; (xxxi) cyano; or (xxxii) a group of formula $X-(CH_2-CH_2-O)_n-CO-O-CH_2-$ wherein n is 1, 2 or 3 and X is amino;

whereby the multiple bond in groups designated under (xxiii), (xxiv) and (xxvi) may not be at the $\beta$-carbon atom of the completed residue I.

Alkyl, alkenyl and alkinyl groups and moieties as or comprised in R, may be branched or straight chain. In general, they will suitably be straight chain and in the case of alkyl, alkenyl and alkinyl groups and moieties directly attaching to the α-carbon atom of the residue I [e.g. the $C_{1-6}$alkyl moiety in ($C_{2-7}$-alkanoyloxy)-($C_{1-6}$alkyl) groups designated under viii)], these are preferably straight-chain. In the case of substituted alkyl, alkenyl or alkinyl groups [e.g. halo-, thio-, amino-, nitro-, cyano- and alkoxy- -alkyl groups], the substituent moiety is preferably in a terminal position on the alkyl, alkenyl or alkinyl moiety. In the case of substituted alkyl groups designated under (v), (Viii), (ix), (x), (xi), (xii) and (xiii), the alkyl moiety which is substituted [e.g. the ($C_{1-6}$alkyl) moiety in ($C_{2-7}$alkanoyloxy)-($C_{1-6}$alkyl) groups under viii)] is preferably methylene.

Furthermore, amino moieties in substituents defined under (iv), (xi), (xii), (xiii), (xx), (xxi), (xxii) and (xxxii) above may be unsubstituted or mono- or di-substituted, e.g. mono- or di-alkyl substituted, for example mono- or di-($C_{1-4}$alkyl)-substituted and/or be in protected form, e.g. as in the case of residues under xxxiii) in which the amino moiety may be e.g. BOC-protected.

In accordance with the above, preferred groups as set forth under (iv), (v), (viii), (ix), (x), (xi), (xii), (xiii), (xviii), (xix), (xx), (xxi), (xxii) and (xxix) above are those of the formulae:

(iv) $R_1-N(R_2)-(CH_2)_a-$;
(v) $R_3-O-CO-NH-CH_2-$;
(viii) $R_4-CO-O-CH_2-$;
(ix) $N_2=(CH_2)_a-CO-O-CH_2-$;
(x) $HO-CO-CH_2-$ and $R_4-O-CO-CH_2-$;
(xi) $R_1-N(R_2)-CO-CH_2-$;
(xii) $R_1-N(R_2)-CO-O-CH_2-$ and $R_1-N(R_2)-(CH_2)_b-CO-O-CH_2-$;
(xiii) $R_1-N(R_2)-(CH_2)_b-O-CO-CH_2-$;
(xviii) $R_5-CO-O-(CH_2)_c-S-$;
(xix) $R_5-CO-O-(CH_2)_c-S(O)_d-$;
(xx) $R_1-N(R_2)-CO-O-(CH_2)_c-S-$ and $R_1-N(R_2)-(CH_2)_e-CO-O-(CH_2)_c-S-$;
(xxi) $R_1-N(R_2)-CO-O-(CH_2)_c-S(O)_d-$ and $R_1-N(R_2)-(CH_2)_e-CO-O-(CH_2)_c-S(O)_d-$;
(xxii) $R_1-N(R_2)-CO-$; and
(xxix) $Aryl-(CH_2)_f-O-CO-NH-CH_2-$;

wherein $R_1$ is hydrogen or $C_{1-4}$alkyl.
$R_2$ is hydrogen or $C_{1-4}$alkyl,
$R_3$ is $C_{1-4}$alkyl,
$R_4$ is $C_{1-6}$alkyl,
$R_5$ is $C_{1-10}$alkyl,
a is an integer from 1 to 6 inclusive,
b is an integer from 1 to 8 inclusive,
c is an integer from 2 to 4 inclusive,
d is 1 or 2,
e is an integer from 1 to 10 inclusive, and
f is an integer from 1 to 4 inclusive.

In the case of residues of formula $R_1-N(R_2)-CO-$ shown above, the amino grouping may additionally comprise an amino acid residue. Thus aminocarbonylalkyl groups under (xi) above also comprise in particular groups of formula

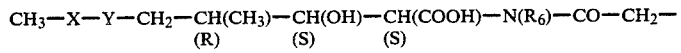

where -x-y- is $-CH_2-CH_2-$ or $-CH=CH-$ (especially TRANS- $-CH=CH-$), $R_6$ is H or $CH_3$ and wherein the hydroxy and carboxy groups may be in protected or unprotected form, e.g. may be methylated.

By "halogen" (or "halo") is meant fluorine (fluoro) chlorine (chloro), bromine (bromo) and iodine (iodo).

Aryl moieties comprised in R are preferably phenyl. Hydroxy substituted aralkyl groups as R may be hydroxy substituted in the aryl or alkyl moiety. Heteroaryl moieties under (xxviii) above include e.g. pyridyl, for example 2-pyridyl.

A group of cyclosporins in accordance with the present invention are those wherein R in formula I has the meanings given under (i) through (iv) inclusive, (vi), (vii), (viii), (x), (xiv) through) (xviii) inclusive, (xxii) through (xxv) inclusive, (xxvii) and (xxx).

A preferred group of cyclosporins in accordance with the present invention are those wherein R in formula I has the meanings given under (i) through (xviii) inclusive, (xx), (xxii) through (xxiv) inclusive, (xxx) and (xxxi). An especially preferred group of cyclosporins in accordance with the present invention are those wherein R in formula I has the meanings given under (i), (viii), (ix), (x), (xiv), (xv) (xvi) and (xxxii). Of these, a sub-group is comprised by those wherein R in formula I has the meanings given under (i), (viii), (x), (xiv) and (xvi).

Further sub-groups of cyclosporins in accordance with the present invention are those wherein R in formula I has the meaning given under (xxx) and those wherein R in formula I has the meaning given under (xxxi).

Specific groups falling within the significances (i) to (xxxii) above are:

(Ia) methyl, ethyl, n-propyl, difluoromethyl, trifluoromethyl or 2,2,2-trifluoroethyl; (Ib) fluoromethyl; (ii) hydroxymethyl, 1-hydroxyethyl, 2-hydroxyethyl or 1-hydroxy-n-hexyl; (iv) aminomethyl, 2-aminoethyl, 3-amino-n-propyl, 4-amino-n-butyl or dimethylaminomethyl; (vi) 2-nitroethyl or cyanomethyl; (vii) methoxymethyl or methylthiomethyl; (viii) acetoxymethyl; (ix) diazoacetoxymethyl; (x) carboxymethyl, methoxycarbonylmethyl or t-butoxycarbonyl methyl; (xi) the group of formula

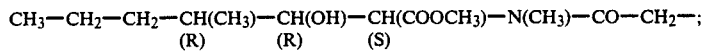

CH$_3$—CH$_2$—CH$_2$—CH(CH$_3$)—CH(OH)—CH(COOCH$_3$)—N(CH$_3$)—CO—CH$_2$—;
                 (R)      (R)      (S)

(xv) methoxycarbonyl; (xvi) methylthio or 2-hydroxyethylthio; (xvii) 2-methoxy-ethylthio; (xviii) 2-acetoxyethylthio; (xxii) aminocarbonyl or methylaminocarbonyl; (xxiii.a) allyl, 2-chloroallyl, 3-chloroallyl, 4,4,4-trifluoro-2-butenyl or propargyl; (xxiii.b) 2-methylallyl or 3,3-dichloroallyl; (xxiv) 1-hydroxy-6-hexenyl; (xxv) benzyl, 2-phenethyl, α-hydroxybenzyl or p-hydroxybenzyl; (xxvii) phenylthio; (xxviii) 2-pyridylthio; (xxx.a) iodine; (xxx.b) fluorine; (xxxi) cyano; or (xxxii) a group of formula X—(CH$_2$—CH$_2$—O)$_n$—CO—O—CH$_2$— wherein n is 2 and X is NH$_2$— or t.C$_4$H$_9$O—CO—NH—.

Amino moieties in the above listing are unsubstituted unless otherwise indicated. The underlined groups may in particular be mentioned. A group of cyclosporins in accordance with the present invention are those wherein R in formula I represents any one of the specific groups designated under (ia), (ii) through (xxii) inclusive, (xxiii.a), (xxiv) through (xxviii) inclusive, (xxxa), (xxxi) and (xxxii) of the above listing.

An especially preferred group of cyclosporins in accordance with the present invention are those of formula II

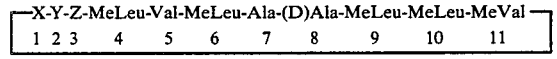

```
 ┌─X-Y-Z-MeLeu-Val-MeLeu-Ala-(D)Ala-MeLeu-MeLeu-MeVal ─┐
 │  1 2 3    4    5     6    7      8     9    10   11 │
 └──────────────────────────────────────────────────────┘
```
(II)

wherein
   X is -MeBmt- or -dihydro-MeBmt-,
   Y is -αAbu-, -Thr-, -Val- or -Nva-, and
   Z is an optically active, α-N-methylated α-amino acid residue having the (D)-configuration.

In formula II, Z is most preferably a residue of formula I as illustrated above wherein R has any of the meanings hereinbefore given.

The residue at the 3-position of the cyclosporins of the invention, e.g. the residue Z in formula II, has the (D)-configuration. While it has been found that the particular process of the present invention as hereinafter described generally favours the preparation of cyclosporins having a residue of the (D)-configuration at the 3-position, corresponding cyclosporins wherein the residue at the 3-position has the (L)-configuration may also be formed to a greater or lesser extent. The present invention is accordingly not restricted to cyclosporins in which the residue at the 3-position has the (D)-configuration exclusively, but is to be understood as including e.g. isomeric mixtures additionally comprising the corresponding enantiomer in which the residue at the 3-position has the (L)-configuration. Where the cyclosporins of the invention are present in admixture with their enantiomer however, it will generally be preferred that the [(L)]$^3$-enantiomer is present in minor proportions only. Most preferably the cyclosporins of the invention will be present in pure or substantially pure [(D)]$^3$-enantiomeric form. Where the process of the invention leads to the production of both [L]$^3$- and [D]$^3$-enantiomeric forms, the individual [D]$^3$-isomer may be purified or separated in accordance with conventional methods, e.g. chromatographically.

In general it appears that the presence of an amino acid residue at the (3)-position in the cyclosporins of the invention is associated with the presence or establishment of a β-turn type II' at this position. Preferred cyclosporins in accordance with the invention are accordingly those wherein the conformation of the peptide chain at the 3-position is that of a β-turn type II'.

In addition to the foregoing the present invention also provides a process for the production of a cyclosporin having an optically active, α-N-methylated α-amino acid residue at the 3-position, said residue having the (D)-configuration, which process comprises:

(a) de-protecting a cyclosporin as aforesaid, said cyclosporin being in protected form;

(b) reacting a polyanion of a cyclosporin having a de-protonated sarcosyl residue at the 3-position, said cyclosporin polyanion being in unprotected or protected form, with an electrophile and, when required, carrying out process step (a);

(c) reducing a cyclosporin in which the residue at the 1-position is -MeBmt- and/or the residue at the 3-position is an optically active, α-N-methylated α-amino acid residue comprising an olefinic or acetylenic linkage, said residue having the (D)-configuration and said cyclosporin being in unprotected or protected form, to produce the corresponding cyclosporin in which the residue at the 1-position is -dihydro-MeBmt- and/or the aforesaid linkage of the residue at the 3-position is saturated and, when required, carrying out process step (a);

(d) subjecting a cyclosporin in which the residue at the 3-position is an optically active, α-N-methylated α-amino acid residue, said residue having the (D)-configuration and said cyclosporin being in unprotected or protected form, to chemical modification so as to convert said residue into another optically active, α-N-methylated α-amino acid residue having the (D)-configuration and, when required, carrying out process step (a).

Process step (a) above can be carried out in accordance with entirely conventional methods known in the art. Protected groups present in the cyclosporin starting material may include e.g. hydroxy-protecting groups at the 3'-OH of the -MeBmt- or -dihydro-MeBmt- residue in the 1-position or at a -Thr- residue in the 2-position, as well as hydroxy-, carboxy- or amino-protecting groups etc . . . present in the residue at the 3-position.

Particular instances of de-protection reactions are hereinafter illustrated in Examples 39 (removal of tetrahydropyranyl OH-protecting group), 43 (removal of t-butoxy carboxy-protecting group) and 47 (removal of acetoxy OH-protecting group).

Electrophiles suitable for use in accordance with process step (b) include halides, in particular bromides and iodides, dithio-compounds, aldehydes, isocyanates, perchlorohalides and $CO_2$. Specific variants of the basic reaction defined under process step (b) above thus include:

(b$^1$) reaction of a polyanion of a cyclosporin as defined under process step (b) above with a compound of formula III

$$R^1-Hal \quad \text{(III)}$$

wherein $R^1$ has the meanings given for R under (i) through (xiv) inclusive, (xxiii) through (xxvi) inclusive, (xxix) and (xxxi) above and Hal is halogen, to produce a cyclosporin wherein the residue at the 3-position is a residue of formula I as hereinbefore illustrated, R has the meanings given for $R^1$ above;

(b$^2$) reaction of a polyanion of a cyclosporin as defined under process step (b) above with a compound of formula IV

$$R^2-S-S-R^2 \quad \text{(IV)}$$

wherein $R^2$ is $C_{1-6}$alkyl, hydroxy-$C_{1-6}$alkyl, ($C_{1-6}$alkoxy)-($C_{1-6}$alkyl), ($C_{2-11}$alkanoyloxy)-($C_{2-4}$alkyl), aminocarbonyl-oxy-($C_{2-4}$alkyl), ($C_{2-11}$aminoalkanoyloxy)-($C_{2-4}$alkyl), aryl or heteroaryl, to produce a cyclosporin wherein the residue at the 3-position is a residue of formula I as hereinbefore illustrated, wherein R has the meanings given under (xvi), (xvii), (xviii), (xx), (xxvii) or (xxviii) above;

(b$^3$) reaction of a polyanion of a cyclosporin as defined under process step (b) above with a compound of formula V

$$R^3-CHO \quad \text{(V)}$$

wherein $R^3$ is $C_{1-5}$alkyl, $C_{3-5}$alkenyl or aryl-$C_{1-5}$alkyl, to produce a cyclosporin wherein the residue at the 3-position is a residue of formula I as hereinbefore illustrated, wherein R is a group of formula $R^3-CH(OH)-$, wherein $R^3$ has the meaning given above [i.e. a group falling within the meanings given for R under (ii), (xxiv) and (xxv) above];

(b$^4$) reaction of a polyanion of a cyclosporin as defined under process step (b) above with carbon dioxide, to produce a cyclosporin wherein the residue at the 3-position is a residue of formula I as hereinbefore illustrated, wherein R is carboxy;

(b$^5$) reaction of a polyanion of a cyclosporin as defined under process step (b) above with a compound of formula VI

$$R^5-N=C=O \quad \text{(VI)}$$

wherein $R^5$ is $C_{1-4}$alkyl, to produce a cyclosporin wherein the residue at the 3-position is a residue of formula I as hereinbefore illustrated, wherein R is a group of formula $R^5-NH-CO-$ [i.e. a group falling within the meaning given for R under (xxii) above]; and (b$^6$) reaction of a polyanion of a cyclosporin as defined under process step (b) above with a halogenating agent, for example a halogen gas or perchlorofluoride, to produce a cyclosporin wherein the residue at the 3-position is halogen, for example fluorine [i.e. as defined under (xxx) above].

Reaction step (b), including each of its variants (b$^1$) through (b$^6$) above, is suitably carried out in an inert solvent or diluent such as tetrahydrofuran at a temperature of from e.g. $-90°$ to $-40°$ C., preferably about $-80°$ C. In each case reaction is completed by quenching of the initially formed ionic species in an aqueous medium. In the case of reaction variant (b$^4$) this is done in an aqueous acid medium, for example in the presence of phosphoric acid as hereinafter described in Example 27.

Where groups $R^1$ or $R^2$ in compounds of formula III and IV include further functional moieties, e.g. amino, hydroxy or carboxy substituents, these may, for the purposes of reaction, conveniently be in protected form. In such cases the initially obtained cyclosporin may subsequently be subjected to deprotection in accordance with process step (a). Alternatively, where e.g. groups $R^1$ include further electrophilic systems, e.g. in the case of polyhalogenated groups $R^1$, the halogen atom X is preferably one providing greater electrophilic attraction (c.f. Example 16 hereinafter).

The product of variant (b$^4$) is relatively unstable and is of interest as an intermediate only, for further derivatisation as described under (d$^1$) below.

The polyanion starting material required for process step (b) is formed transitorily in situ in the reaction medium and is prepared by treatment of a protected or unprotected cyclosporin having a sarcosyl residue at the 3-position (for example a cyclosporin having the formula II as illustrated above, wherein X is -MeBmt- or -dihydro-MeBmt- each in unprotected or O-protected form, Y has the meaning given for formula II and Z is -Sar-) with an appropriate base. Suitable bases are e.g. alkali metal amides, in particular lithium, sodium and potassium dialkylamides, for example lithium diisopropylamide.

The deprotonated sarcosyl residue may conveniently be represented as having the formula

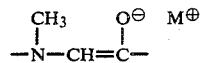

$$-\overset{CH_3}{\underset{|}{N}}-CH=\overset{O^\ominus \quad M^\oplus}{\underset{|}{C}}-$$

wherein M is an alkali metal, e.g. lithium, ion.

Formation of the polyanion proceeds with de-protonation at free-hydroxy groups and non-methylated α-N-atoms with the cyclosporin molecule prior to de-protonation at the sarcosyl residue in the 3-position. Accordingly, in addition to de-protonation at the 3-position, the said polyanion will also be de-protonated at other residues within the cyclosporin molecule having such free —OH and α—NH— groupings. Thus where the polyanion is the polyanion of a cyclosporin having the formula II as illustrated above wherein X and Y have the meanings given for formula II and Z is -Sar-, the polyanion will also exhibit de-protonation at the 1-position (3'—OH of the residue -MeBmt- or -dihydro-MeBmt-) at the 2-position (OH if B is -Ser-/at the α-N-atom), and at the 5-, 7- and 8-positions (α-N-atoms). Since the sarcosyl residue at the 3-position is the least susceptible to de-protonation, the amount of base required for polyanion formation will correspond to ca. at least 1.1 equivalent per unprotected —OH group and non-methylated α-N-atom and for the -Sar$^3$- residue. Similarly the total degree of de-protonation (i.e. the number of negative charges present) will be proportional to the number of unprotected —OH groups and non-methylated α-N-atoms present in addition to said -Sar³- residue.

Thus for the preparation of the required polyanion starting material corresponding to formula II, the minimum amount of base required will be: ca. 1.1 equivalent (for deprotonation of the 3'—OH of the -MeBmt- or -dihydro-MeBmt- residue A, in the event that this is in unprotected form), plus 4.4 equivalents (for deprotonation of the non-methylated α-N-atoms of the residues at the 2-, 5-, 7- and 8-positions), plus 1.1 equivalent (for deprotonation of the hydroxy group at the 2-position, in the event that this is -Thr- in unprotected form), plus 1.1 equivalent for deprotonation of the -Sar- residue at the 3-position, giving a total of from ca. 5.5 to 7.7 equivalents. The obtained polyanion will correspondingly bear from 5 to 7 negative charges [at positions (1), 2, (2), 3, 5, 7 and 8]. In particular instances however, in order to reduce viscosity of the reaction mixture, it may be advantageous to employ excess base e.g. in amounts of up to ca. 2× the theoretical minimum needed, e.g. for preparation of polyanion starting materials required for the production of cyclosporins of formula II, ca. 11 to 16 equivalents.

Polyanion starting materials required for the production of cyclosporins of formula II may be represented by formula VII

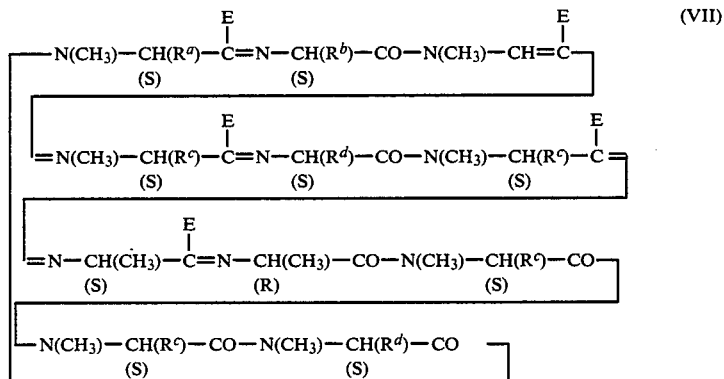

(VII)

wherein $R^a$ has the formula $CH_3$—x-y-$CH_2$—$CH(CH_3)$—$CH(R^e)$—
                                           (R)          (R)

in which -x-y- is —CH=CH—(trans) or —CH$_2$—CH$_2$— and $R^e$ is hydroxy in protected form or is E, $R^b$ is $C_2H_5$—,

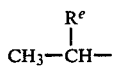

wherein $R^e$ has the meaning given above, i.$C_3H_7$— or n$C_3H_7$—,
$R^c$ is i.$C_4H_9$—, $R^d$ is i.$C_3H_7$— and
E is [—O⊖M⊕] in which M⊕ is an alkali metal ion in particular Li⊕.

Process step (c) may be carried out analogously to known methods, e.g. for reducing naturally-occurring cyclosporins to the corresponding dihydro-cyclosporins, for example by catalytic hydrogenation, e.g. analogously to the general methods disclosed in UK Patent Specification No. 1,567,201. Suitably hydrogenation is effected under neutral pH conditions at temperatures of from ca. 20° C. to ca. 30° C., at atmospheric or slightly elevated pressure, in the presence of a catalyst such as platinum, palladium (e.g. palladium on charcoal) or tris-(triphenylphosphin)-rhodium(I) chloride in the presence of an inert solvent or diluent such as ethyl acetate, lower aliphatic alkanols such as methanol or isopropanol, benzene, acetone or mixtures thereof. It will be appreciated that in carrying out process step (c) to reduce e.g. -MeBmt- groups to -dihydro-MeBmt-, groups susceptible to reduction or reductive cleavage at the 3-position, may also undergo reaction. Thus alkenyl and alkinyl groups as R in formula III may undergo concommitant reduction e.g. to alkyl, as for example described in Example 37 hereinafter.

Process step (c) may accordingly be employed e.g.

(c¹) for the production of cyclosporins of formula II as hereinbefore illustrated wherein X is -dihydro-MeBmt-, Y has the meanings given for formula II and Z is a residue of formula I as hereinbefore defined, by reduction or selective reduction of the corresponding cyclosporin of formula II wherein X is -MeBmt-; or (c²) for the production of cyclosporins of formula II as hereinbefore illustrated wherein X is -dihydro-MeBmt-, Y has the meanings given for formula II and Z is a residue of formula I as hereinbefore illustrated wherein R is $C_{3-6}$alkyl, halo-substituted $C_{3-6}$alkyl, hydroxy-$C_{3-6}$alkyl, aryl-$C_{3-6}$alkyl or hydroxy-substituted aryl-($C_{3-6}$alkyl), by reduction of the corresponding cyclosporins of formula II wherein X is -MeBmt- or -dihydro-MeBmt- and Z is a residue of formula I as hereinbefore illustrated wherein R has the meanings given under (xxiii), (xxiv) or (xxvi) above.

Possible conversions in accordance with process step (d) include e.g.

(d¹) reaction of a cyclosporin wherein the residue at the 3-position is a residue of formula I as hereinbefore illustrated, wherein R is carboxy (e.g. an immediate reaction product of process variant b⁴) with a $C_{1-6}$alkylating agent, to produce a corresponding cyclosporin wherein R has the meanings given under (xv) above;

(d²) oxidising a cyclosporin wherein the residue at the 3-position is a residue of formula I as hereinbefore illustrated, wherein R has the meaning given under (xviii) or (xx) above, to produce a corresponding cyclosporin, wherein R has the meanings given under (xix) or (xxi) above;

(d³) subjecting a cyclosporin wherein the residue at the 3-position is a residue of formula I as hereinbefore illustrated, wherein R is (C$_{2-7}$alkanoyloxy)-(C$_{1-6}$alkyl) [c.f. (viii) above], to reductive cleavage, to produce a corresponding cyclosporin wherein R has the meaning given under (ii) above;

(d$^4$) subjecting a cyclosporin wherein the residue at the 3-position is a residue of formula I as hereinbefore illustrated, wherein R is (C$_{1-6}$alkoxy)-(C$_{1-6}$alkyl) or (C$_{1-6}$alkoxy)-(C$_{1-6}$-alkylthio) [c.f. (vii) and (xvii) above] or hydroxy-(C$_{1-6}$alkyl) or hydroxy-(C$_{1-6}$alkylthio) each in hydroxy protected form, to ether cleavage or other de-protective means, to produce a corresponding cyclosporin wherein R has the meanings given under (ii) or (xvi) above;

(d$^5$) hydrolysing a cyclosporin wherein the residue at the 3-position is a residue of formula I as hereinbefore illustrated, wherein R is (C$_{2-7}$alkoxycarbonyl)-(C$_{1-6}$alkyl) or (C$_{2-5}$alkoxycarbonylamino)-(C$_{1-4}$alkyl) [c.f. (x) and (v) above] to produce a corresponding cyclosporin wherein R is carboxy-(C$_{1-6}$alkyl) or amino-(C$_{1-4}$alkyl) [c.f. (x) and (iv) above];

(d$^6$) esterifying a cyclosporin wherein the residue at the 3-position is a residue of formula I as hereinbefore illustrated wherein R is carboxy-(C$_{1-6}$alkyl) or carboxy-(C$_{1-4}$alkyl) [c.f. (x) above] so as to produce a corresponding cyclosporin wherein R is (C$_{2-7}$alkoxycarbonyl)-(C$_{1-6}$alkyl) or amino-(C$_{2-9}$-alkoxycarbonyl)-(C$_{1-4}$alkyl) in amino-protected form [c.f. (x) and (xiii) above], and when required, carrying out process step (a) hereinabove;

(d$^7$) reacting a cyclosporin wherein the residue at the 3-position is a residue of formula I as hereinbefore illustrated wherein R is hydroxymethyl [c.f. (ii) above] with a compound of formula VIII

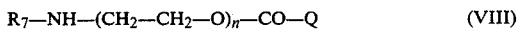

$$R_7-NH-(CH_2-CH_2-O)_n-CO-Q \quad (VIII)$$

wherein R$_7$ is an amino protecting group (e.g. BOC), n is 1, 2 or 3 and Q is a leaving group, so as to produce a corresponding cyclosporin wherein R is a group of formula IX

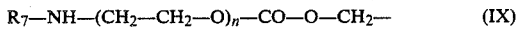

$$R_7-NH-(CH_2-CH_2-O)_n-CO-O-CH_2- \quad (IX)$$

wherein R$_7$ and n have the meanings given above [c.f. (xxxiii) above];

(d$^8$) reacting a cyclosporin wherein the residue at the 3-position is a residue of formula I as hereinbefore illustrated wherein R is hydroxy-(C$_{1-6}$alkyl) [c.f. (ii) above] with a compound of formula X

$$R_8-CO-Q \quad (X)$$

wherein R$_8$ is C$_{1-6}$alkyl or diazo-(C$_{1-6}$alkyl) and Q is a leaving group to produce a corresponding cyclosporin wherein R has the meaning given under (viii) or (ix) above;

(d$^9$) reacting a cyclosporin wherein the residue at the 3-position is a residue of formula I as hereinbefore illustrated wherein R is hydroxy-(C$_{1-6}$alkylthio) [c.f. (xvi) above] with a compound of formula XI

$$R_9-CO-Q \quad (XI)$$

wherein R$_9$ is C$_{1-10}$alkyl or amino-(C$_{1-10}$alkyl) in which the amino moiety is in protected form, so as to produce a corresponding cyclosporin wherein R is (C$_{2-11}$alkanoyloxy)-(C$_{2-4}$-alkylthio) or (C$_{2-11}$aminoalkanoyloxy)-(C$_{2-4}$alkylthio) [c.f. (xviii) and (xx) above] and, when required, carrying out process step (a) hereinabove;

(d$^{10}$) converting a cyclosporin wherein the residue at the 3-position is -(D)MeSer- [c.f. (ii) above] into the corresponding cyclosporin wherein the residue at the 3-position is a residue of formula I as hereinbefore illustrated, wherein R is halomethyl [c.f. (i) above], for example fluoromethyl, e.g. by reaction with (diethylamino)-sulfur-trihalide, e.g., the trifluoride.

Each of above variants (d$^1$) through (d$^{10}$) may be carried out in accordance with conventional methods known in the art. Yet further possible interconversions will be apparent to the skilled worker.

Variant (d$^1$) is conveniently conducted in situ immediately following reaction in accordance with variant (b$^4$). Suitable alkylating agents include any of those known in the art, including e.g. C$_{1-6}$alkylhalides. For the purposes of methylation, reaction is suitably carried out employing diazomethane in the presence of an inert solvent or diluent such as ethyl ether at ambient or slightly elevated temperature, e.g. as hereinafter described in Examples 27 through 30.

Variant (d$^2$) may be carried out e.g. employing peracids, H$_2$O$_2$ or MnO$_2$ as oxidising agent, in an inert solvent or diluent e.g. such as methylene chloride and lower alkanols such as methanol, for example at a temperature of from −20° to 50° C.

Variant (d$^3$) may be carried out e.g. employing lithium aluminium hydride as reducing agent in an inert solvent such as tetrahydrofuran at a temperature of from e.g. 0° to 40° C.

Variant (d$^4$) may be carried out e.g. in an acid medium at temperatures of e.g. 15° C. to 40° C. Examples of hydroxy protecting groups include e.g. the tetrahydropyranyl group. The general procedures are illustrated in Example 39 hereinafter.

Hydrolysis in accordance with variant (d$^5$) is illustrated e.g. in Example 43 hereinafter. As applied to cyclosporins wherein R is (C$_{2-5}$alkoxycarbonylamino)-(C$_{1-4}$alkyl) this process embraces e.g. standard procedures for the de-protection of BOC-protected amino groups.

Variant (d$^6$) may be carried out in accordance with conventional esterification techniques. Thus methyl esters may be obtained analogously to process step (d$^1$) employing e.g. diazomethane as co-reactant and proceeding for example as hereinafter described in Example 44.

The method of variant (d$^7$) may suitably be carried out using the free acid of formula X (Q=OH) as starting material and effecting reaction in the presence of a castro reagent as hereinafter described in Example 49. For the purposes of reaction the terminal amino group is suitably in protected form, e.g. BOC-protected form. The BOC-protected products also possess pharmaceutical activity as hereinafter described, so that subsequent deprotection is optional.

Variants (d$^8$) and (d$^9$) may be carried out in accordance with entirely conventional acylation techniques, e.g. employing acid halides or anhydrides of formula X or XI (Q=halogen, R$_8$—CO—O— or R$_9$—CO—O), suitably in the presence of an acid binding agent such as pyridine at ambient temperature, e.g. as hereinafter illustrated in Examples 40 through 42.

Variant (d$^{10}$) is illustrated in following Example 47. In order to avoid unwanted side reaction, e.g. at the 3'—OH group of the -MeBmt- or -dihydro-MeBmt-residue, this is conveniently first converted into protected form and de-protection effected subsequent to step variant (d¹⁰), e.g. as hereinafter described in Examples 45, 46 and 48.

The cyclosporin polyanion starting materials hereinbefore described with reference to process step (b) are also new and also form part of the present invention. Accordingly in a particular aspect the present invention also provides:

(i) A cyclosporin polyanion having a de-protonated sarcosyl residue at the 3-position;

(ii) A polyanion according to (i) which is a polyanion of a cyclosporin having the formula II as hereinbefore illustrated, wherein X and Y have the meanings given for formula II and Z is -Sar-;

(iii) A polyanion according to (ii) which is a polyanion of Cyclosporine, [Thr]²-Cyclosporine, [Val]²-Cyclosporine or [Nva]²-Cyclosporine;

(iv) A polyanion according to (ii) which is a polyanion of [Dihydro-MeBmt]¹-Cyclosporine or [Dihydro-MeBmt]¹-[Val]²-Cyclosporine;

(v) A polyanion according to (i) having the formula VII as hereinbefore defined, in particular a polyanion having the formula VII as hereinbefore defined but wherein $R^e$ is E.

[As will be appreciated, polyanions under (ii), (iii) and (iv) above are polyanions corresponding to or derived from the cyclosporin defined, i.e. in the case of polyanions defined under (ii), a polyanion of a cyclosporin of formula II, wherein the residue -Sar- as Z is de-protonated].

In addition the present invention also provides:

(vi) a method for the production of a cyclosporin polyanion as defined under (i) through (v) above, which method comprises treating a cyclosporin, for example a cyclosporin of formula II as hereinbefore illustrated, wherein X and Y have the meanings given for formula II and Z is -Sar-, with a sufficient amount of an alkali metal amide, for example lithium diisopropyl amide, to effect deprotonation of the sarcosyl residue in the 3-position, e.g. in relation to formula II to effect deprotonation of the residue Z.

Methods for effecting the above process are as hereinafter described.

The following Examples are illustrative of the processes for the production of the compounds of the invention. By -3'-Acetoxy-MeBmt- as employed in Examples 45, 46 and 47 is meant the residue of formula

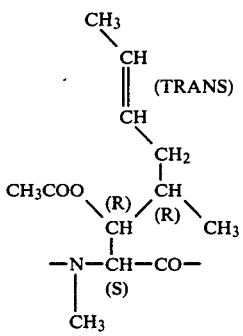

EXAMPLE 1

Synthesis of [(D)MeAla]³-Cyclosporine: Formula IIa below, X=-MeBmt-, Y=-αAbu-, R=—CH₃

0.83 m mol. Cyclosporine (cyclosporin A) in 15 ml Tetrahydrofuran are added drop-wise over ca. 2 min. to a solution of 6.7 equivalents of lithiumdiisopropylamide in 50 ml tetrahydrofuran at −78° C. The reaction mixture is stirred for 1 hour at −78° C. and 12 m mol. methyliodide are added, also at −78° C. The reaction mixture is allowed to rise to ambient temperature and is then poured into a 2N solution of NH₄Cl. This solution is extracted with ethyl ether dried over MgSO₄ and evaporated. The title compound is recovered following chromatographic purification employing silica gel and ethyl ether/methanol as eluant: $[\alpha]_D^{20} = -239°$, c=1 in CHCl₃.

The following cyclosporins of formula IIa may be prepared analogously:

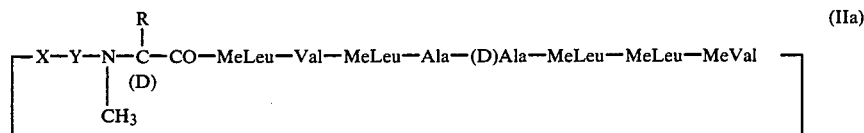

| EXAMPLE | X | Y | R | Physical Data |
|---|---|---|---|---|
| 2 | —MeBmt— | —Nva— | CH₃— | $[\alpha]_D^{20} = -212.4°$<br>c = 0.48 in CHCl₃ |
| 3 | —MeBmt— | —Thr— | CH₃— | $[\alpha]_D^{20} = -224.3°$<br>c = 0.46 in CHCl₃ |
| 4 | —MeBmt— | —Val— | CH₃— | $[\alpha]_D^{20} = -215.5°$<br>c = 0.5 in CHCl₃ |
| 5 | —MeBmt— | —αAbu— | C₂H₅— | foam |
| 6 | —MeBmt— | —αAbu— | ⟨phenyl⟩—CH₂— | $[\alpha]_D^{20} = -224.0°$<br>c = 0.825 in CHCl₃ |
| 7 | —MeBmt— | —αAbu— | CH₂=CH—CH₂— | $[\alpha]_D^{20} = -202.0°$<br>c = 0.5 in CHCl₃ |
| 8 | —MeBmt— | —Val— | CH₂=CH—CH₂— | $[\alpha]_D^{20} = -190.0°$<br>c = 0.72 in CHCl₃ |
| 9 | —MeBmt— | —Nva— | CH₂=CH—CH₂— | $[\alpha]_D^{20} = -180.0°$ |

-continued

| EXAMPLE | X | Y | R | Physical Data |
|---------|---|---|---|---------------|
| 10 | —DihydroMeBmt— | —αAbu— | $CH_2=CH-CH_2-$ | $[\alpha]_D^{20} = -193.0°$<br>c = 0.5 in $CHCl_3$ |
| 11 | —DihydroMeBmt— | —Val— | $CH_2=CH-CH_2-$ | $[\alpha]_D^{20} = -200.0°$<br>c = 0.5 in $CHCl_3$ |
| 12 | —MeBmt— | —αAbu— | $CH\equiv C-CH_2-$ | $[\alpha]_D^{20} = -214.0°$<br>c = 1.06 in $CHCl_3$ |
| 13 | —MeBmt— | —αAbu— | CIS $Cl-CH=CH-CH_2-$ | $[\alpha]_D^{20} = -236.0°$<br>c = 0.5 in $CHCl_3$ |
| 14 | —MeBmt— | —αAbu— | TRANS $Cl-CH=CH-CH_2-$ | $[\alpha]_D^{20} = -218.0°$<br>c = 0.5 in $CHCl_3$ |
| 15 | —MeBmt— | —αAbu— | $Cl_2C=CH-CH_2-$ | $[\alpha]_D^{20} = -222.0°$<br>c = 0.5 in $CHCl_3$ |
| 16 | —MeBmt— | —αAbu— | $CH_2=CCl-CH_2-$ | $[\alpha]_D^{20} = -199.0°$<br>c = 0.5 in $CHCl_3$ |
| 17 | —MeBmt— | —αAbu— | $CH_2=C(CH_3)-CH_2-$ | $[\alpha]_D^{20} = -200.7°$<br>c = 0.5 in $CHCl_3$ |
| 18 | —MeBmt— | —αAbu— | —CN | $^1H$—NMR $COCl_3$,<br>360 Mz, 20° C.<br>5.87 [S,1H,H—C(2³)] |
| 19 | —MeBmt— | —αAbu— | $t.C_4H_9O-CO-CH_2-$ | $[\alpha]_D^{20} = -202.0°$<br>c = 1 in $CHCl_3$ |
| 20 | —MeBmt— | —αAbu— | $(CH_3)_2N-CH_2-$ | foam |

Halide starting material=R-Hal in which:
Hal=I—Examples 1 to 5 and 16 above;
Hal=Br—Examples 6 to 15 and 17 to 20 above.

EXAMPLE 21

Synthesis of [Val]²-[(D)Methylthio-Sar]³-Cyclosporine: Formula IIa, X=-MeBmt-, Y=-Val-, R=CH₃—S—.

4.1 g [Val]²-Cyclosporine (cyclosporin D) are dissolved in 3.2 liters tetrahydrofuran and cooled to −83° C. 3.95 ml of a 0.57 molar solution of lithiumdiisopropylamine in hexane are then added drop-wise over 1 hour at −83° to −80° C. and the reaction mixture stirred for 1 hour at −80° C. 34.7 g dimethyldisulfide are then added drop-wise over 1 hour at −80° C. and the temperature is then allowed to rise to −10° C. over 1 hour and the reaction mixture subsequently stirred for 30 mins. at room temperature. The reaction mixture is extracted with 4 liters ethyl ether and 3 liters KHCO₃ (20%) and the ether phase evaporated. The residue is purified chromatographically using 2.5 kg silica gel (0.04–0.063 mm) and aqueous ethyl acetate as eluant to yield the title compound: $[\alpha]_D^{20} = -209.34°$ (c=0.514 in CHCl₃).

The following compounds of formula IIa may be prepared analogously:

| EXAMPLE | X | Y | R | PHYSICAL DATA |
|---------|---|---|---|---------------|
| 22 | —MeBmt— | —Nva— | $CH_3-S-$ | $[\alpha]_D^{20} = -200.0°$<br>c = 0.52 in $CHCl_3$ |
| 23 | —MeBmt— | —αAbu— | $CH_3-S-$ | $[\alpha]_D^{20} = -213.0°$<br>c = 1 in $CHCl_3$ |
| 24 | —MeBmt— | —αAbu— | 2-pyridyl-S— | $[\alpha]_D^{20} = -244.0°$<br>c = 0.5 in $CHCl_3$ |
| 25 | —MeBmt— | —αAbu— | phenyl-S— | $[\alpha]_D^{20} = -220.0°$<br>c = 0.965 in $CHCl_3$ |
| 26 | —MeBmt— | —αAbu— | S/R 1,4-dioxaspiro ring —O—CH₂—CH₂—S— | 1H—NMR(CDCl₃), 360 MHz, 20° C.):<br>6.06–6.09 [2s,1H, H—C (2³)] |

EXAMPLE 27

Synthesis of [(D)Methoxycarbonyl-Sar]³-Cyclosporine: Formula IIa, X=-MeBmt-, Y=-αAbu-, R=CH₃O—CO—.

The reaction is carried out analogously to Example 1, first by reaction of Cyclosporine with lithiumdiisopropylamide. Dry $CO_2$ is subsequently passed into the reaction mixture for 15 minutes. After passage of the $CO_2$ the reaction mixture is allowed to react for a further hour at −80° C. The reaction mixture is then poured into 2N aqueous phosphoric acid and the whole extracted with ethyl ether. The ether solution is concentrated and reacted with a solution of diazomethane in ethyl ether until the yellow coloration remains. The obtained reaction mixture is evaporated and the residue purified chromatographically, to yield the title compound. m.p.=120°-130° C.

The following compounds of formula IIa may be prepared analogously:

| EXAMPLE | X | Y | R | PHYSICAL DATA |
|---|---|---|---|---|
| 28 | -MeBmt- | -Val- | CH₃O—CO— | $[\alpha]_D^{20} = -192.2°$ c = 0.41 in CHCl₃ |
| 29 | -MeBmt- | -Thr- | CH₃O—CO— | $[\alpha]_D^{20} = -204.6°$ c = 0.5 in CHCl₃ |
| 30 | -MeBmt- | -Nva- | CH₃O—CO— | $[\alpha]_D^{20} = -200.7°$ c = 0.5 in CHCl₃ |

EXAMPLE 31

Synthesis of [(D)MeSer]³-Cyclosporine: Formula IIa, X=-MeBmt-, Y=-αAbu-, R=HO—CH₂—.

Reaction is carried out analogously to Example 1 but employing a mixture of monomeric formaldehyde in tetrahydrofuran (obtained from paraformaldehyde and tetrahydrofuran in the presence of a catalytic amount of borontrifluoride etherate) in place of methyl iodide as co-reactant.

$[\alpha]_D^{20}$ for the title compound=−213.0°, c=1 in CHCl₃.

EXAMPLE 34

Synthesis of [(D)Methylaminocarbonyl-Sar]³-Cyclosporine: Formula IIa, X=-MeBmt-, Y=-αAbu-, R=CH₃—NH—CO—, The title compound is produced analogously to Example 1, but employing methylisocyanate in place of methyliodide as co-reactant: $[\alpha]_D^{20} = -174.0°$, c=0.9 in CHCl₃.

EXAMPLE 35

Synthesis of [(D)Fluor-Sar]³-Cyclosporine: Formula IIa, X=-MeBmt-, Y=-αAbu-, R=F.

1.2 g Cyclosporine (cyclosporin A) in 20 ml tetrahydrofuran are added drop-wise at −78° C. over 3 mins. to 6.7 equivalents of lithiumdiisopropylamide in 80 ml tetrahydrofuran and the reaction mixture is stirred for 1 hour at −78° C. A strong stream of perchlorylfluoride (FClO₃) is passed through the reaction mixture for 3 mins. at −78° C. The temperature is allowed to rise over 3 hours to −30° C. and poured onto 20 ml H₂O and washed with ethyl ether. The ether phase is evaporated and the residue purified on 220 g silica gel (0.040-0.030 mm) using (a) 2500 ml ethyl ether/methanol (98:2) followed by (b) 1500 ml ethyl ether/methanol (97:3) as eluant. The title compound is recovered as the more polar fraction from fractions obtained during elution step (b): $[\alpha]_D^{20} = -245°$, c=1.02 in CHCl₃.

EXAMPLE 36

Synthesis of [Dihydro-MeBmt]¹-[Val]²-[(D)Methylthio-Sar]³-Cyclosporine: Formula IIa, X=-Dihydro-MeBmt-, Y=-Val-, R=CH₃—S—.

6 g of the product of Example 21 are hydrogenated in the presence of 6 g tris-(triphenylphospin)-rhodium(I) chloride in 150 ml benzene and 75 ml acetone as solvent. The product solution is concentrated and purified chromatographically employing silica gel and hexane/acetone as eluant to yield the title compound: $[\alpha]_D^{20} = -193.94$, c=0.545 in CHCl₃.

The following compounds of formula IIa may be obtained analogously from the indicated starting material.

| EXAMPLE | STARTING MATERIAL = PRODUCT OF EXAMPLE | X | Y | R | PHYSICAL DATA |
|---|---|---|---|---|---|
| 37 | 10 | -Dihydro-MeBmt- | -αAbu- | C₃H₇- | $[\alpha]_D^{20} = -204°$ c = 0.5 in CHCl₃ |
| 38 | 11 | -Dihydro-MeBmt- | -Val- | C₃H₇- | $[\alpha]_D^{20} = -192°$ c = 0.5 in CHCl₃ |

The following compounds of formula IIa may be prepared analogously employing the corresponding aldehyde of formula R—CHO as co-reactant.

EXAMPLE 39

Synthesis of [(D)2-Hydroxy-ethylthio-Sar]³-Cyclosporine: Formula IIa, X=-MeBmt-, Y=-αAbu-, R=HO—(CH₂)₂—S—.

| EXAMPLE | X | Y | R | PHYSICAL DATA |
|---|---|---|---|---|
| 32 | —MeBmt— | —αAbu— | CH₃—CH(OH)— | 1H—NMR (CDCl₃, 360 MHz, 20° C.): 4.77 [d,J = 7.2, 1H, H—C (2³) |
| 33 | —MeBmt— | —αAbu— | 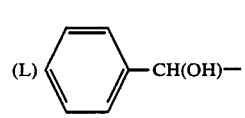 | m.p. = 162-167° C. |

90 mg of the product of Example 26 are added to 0.5 ml acetic acid/H$_2$O/tetrahydrofuran (3:1:1) and stirred for 48 hours at room temperature. The reaction mixture is neutralised with saturated NaHCO$_3$ and extracted with ethyl ether. The ether phase is evaporated and the residue purified chromatographically to yield the title compound: $[\alpha]_D^{20} = -187.0°$, c=0.86 in CHCl$_3$.

EXAMPLE 40

Synthesis of [(D)2-Acetoxy-ethylthio-Sar]$^3$-Cyclosporine: Formula IIa, X=-MeBmt-, Y=-αAbu-, R=CH$_3$CO—O—(CH$_2$)$_2$—S—.

100 mg of the product of Example 39 are added to 30 μl acetic anhydride in 1 ml pyridine. The reaction mixture is stirred for 5 hours at room temperature and then diluted with ethyl ether and washed with saturated aqueous NaCl. The ether solution is evaporated and the residue purified chromatographically to yield the title compound: $[\alpha]_D^{20} = -186.0°$, c=1.34 in CHCl$_3$.

The following compounds of formula IIa, may be prepared analogously from the indicated starting material.

EXAMPLE 46

Synthesis of [3'-Acetoxy-MeBmt]'-[(D)MeSer]$^3$-Cyclosporine: Formula IIa, X=-3'-Acetoxy-MeBmt-, Y=-αAbu-, R=HO—CH$_2$—.

0.58 ml 1% K$_2$CO$_3$ is added to 50 mg of the product of Example 45 dissolved in 7.5 ml ethanol. The reaction mixture is allowed to stand for 2 hours at room temperature and then taken up in ethyl ether. The ether phase is washed with water and evaporated to yield the title compound: $[\alpha]_D^{20} = -259°$ C., c=1.0 in CHCl$_3$.

EXAMPLE 47

Synthesis of [3'-Acetoxy-MeBmt]$^1$-[(D)Fluoromethyl-Sar]$^3$-Cyclosporine: Formula IIa, X=-3'-Acetoxy-MeBmt-, Y=-αAbu-, R=F—CH$_2$—.

A solution of 0.1 ml (diethylamino)-sulfur-trifluoride (DAST) is added to a solution of 500 mg of the product of Example 46 in 10 ml methylenechloride, pre-cooled to $-20°$ C. The reaction mixture is allowed to react for 30 mins. at $-20°$ C., 10 ml saturated NaHCO$_3$ in H$_2$O are added and the whole extracted with ethyl ether.

| EXAMPLE | START. MAT. = PROD OF EX. | X | Y | R | PHYSICAL DATA |
|---|---|---|---|---|---|
| 41 | 31 | -MeBmt- | -αAbu- | CH$_3$CO—O—CH$_2$ | RF = 0.5 in CH$_2$Cl$_2$: CH$_3$OH (9:1) on silica gel |
| 42 | 31 | -MeBmt- | -αAbu- | N$_2$=CH—CO—O—CH$_2$- | JR (CH$_2$Cl$_2$) 2120cm$^{-1}$( ) |

EXAMPLE 43

Synthesis of [(D)MeAsp]$^3$-Cyclosporine: Formula IIa, X=-MeBmt-, Y=-αAbu-, R=HOOC—CH$_2$—.

400 mg of the product of Example 19 are reacted with 16 ml trifluoroacetic acid at 0° C. After 2 hours the reaction mixture is concentrated under vacuum, the residue taken up in ethyl ether and washed with NaHCO$_3$. The ether phase is evaporated to yield the title compound: 1H-NMR (CDCl$_3$, 360 MHz, 20° C.): 5.30 [m,4H, H-C (2$^3$), H-C (2$^4$), H-C (6$^1$), H-C (7$^1$)].

EXAMPLE 44

Synthesis of [(D)Methoxycarbonylmethyl-Sar]$^3$-Cyclosporine: Formula IIa, X=-MeBmt-, Y=-αAbu-, R=CH$_3$O—CO—CH$_2$—.

Diazomethane in solution is added to 100 mg of the product of Example 43 until the reaction remains yellow. The reaction mixture is evaporated and the residue purified chromatographically to yield the title compound: $[\alpha]_D^{20} = -225.0°$, c=1 in CHCl$_3$.

EXAMPLE 45

Synthesis of [3'-Acetoxy-MeBmt]$^1$-[(D)O-Acetyl-MeSer]$^3$-Cyclosporine: Formula IIa, X= −3'-Acetoxy-MeBmt-, Y=-αAbu-, R=CH$_3$CO—O—CH$_2$—.

200 mg of the product of Example 31 are dissolved in 1 ml pyridine and 5 mg dimethylaminopyridine and 1 ml acetic acid anhydride are added at 5° C. The reaction mixture is allowed to stand for 18 hours at room temperature and then concentrated. The residue is taken up in ethyl ether and washed with dilute HCl, NaHCO$_3$ and H$_2$O. The ether phase is evaporated to yield the title compound: $[\alpha]_D^{20} = -258°$ C., c=1.0 in CHCl$_3$.

The ether phase is evaporated and the residue purified chromatographically to yield the title compound: 1H-NMR (CDCl$_3$, 360 MHz, 20° C.): 5.15 [m, 3H, H-C (2$^3$), H-C (2$^6$)].

EXAMPLE 48

Synthesis of [(D)Fluoromethyl-Sar]$^3$-Cyclosporine: Formula IIa, X=-MeBmt-, Y=-αAbu-, R=F—CH$_2$—.

2.2 ml hydrazine hydrate are added to 330 mg of the product of Example 47 in 6 ml ethanol and the reaction mixture stirred at 60° C. under argon, and then re-cooled to 10° C. The reaction mixture is partitioned between saturated NaHCO$_3$ in H$_2$O and ethyl ether and the aqueous phase re-extracted with ethyl ether. The combined ether phases are washed with H$_2$O and evaporated. The residue is purified chromatographically to yield the title compound: $[\alpha]_D^{20} = -192.5°$, c=1.00 in CHCl$_3$.

EXAMPLE 49

Synthesis of [(D)-2(2-BOC-amino-ethoxy)-ethoxy-acetoxymethyl-Sar]$^3$-Cyclosporine: Formula IIa, X=-MeBmt-, Y=-αAbu-, R=t.C$_4$H$_9$O—CO—NH—(CH$_2$)$_2$—O—(CH$_2$)$_2$—O—CH$_2$—CO—O—CH$_2$—.

125 mg of the product of Example 31 in 2 ml methylene chloride are added to 11 μl N-methyl-morpholine, 44.2 mg "Castro-reagent" and 30 mg 2(2-t.butoxycarbonylamino-ethoxy)-ethoxy-acetic acid [BOC—NH—(CH$_2$—CH$_2$—O)$_2$—CH$_2$—COOH]. The reaction mixture is stirred for 60 hours at room temperature, concentrated and the residue taken up with ethyl ether and washed with H$_2$O. The ether phase is evaporated and the residue purified chromatographically to yield the title compound: $[\alpha]_D^{20} = -190.0$, c=1.0 in CHCl$_3$.

EXAMPLE 50

Proceeding analogously to Example 49 but employing the product of Example 43 as cyclosporin starting material and the compound of formula $$CH_3-(CH_2)_5-CH(CH_3)-CH(OH)-CH(COOCH_3)-NH-CH_3$$
$$\phantom{CH_3-(CH_2)_5-}(R)\phantom{HHHH}(R)\phantom{HHHH}(S)$$

as co-reactant there is obtained
The compound of formula IIa wherein
X = -MeBmt-,
Y = -αAbu-, and
R = CH$_3$—(CH$_2$)$_3$—CH(CH$_3$)—CH(OH)—CH(COOCH$_3$)—N(CH$_3$)—CO—CH$_2$—;
$[\alpha]_D^{20} = -176°$, c=0.975 in CHCl$_3$.

End-product cyclosporins of the present invention (e.g. excluding cyclosporin polyanions and other intermediates hereinbefore described) hereinafter referred to as "product cyclosporins", and in particular cyclosporins of formula II as hereinbefore illustrated wherein X and Y have the meanings given for formula II and Z is a residue of formula I as hereinbefore defined, possess pharmaceutical utility as may be demonstrated, e.g. in the following test methods.

1. Immunosuppressive activity:
1.1 Local heamolysis in vitro in gel [R. I. Mishell and R. W. Dutton, J. Exp. Medicine, 126, 423 442 (1976)]:

"Product cyclosporins" inhibit haemolysis zones compared with untreated controls at concentrations of from 0.01 to 10 μg/ml.

1.2 Lymphocyte stimulation test according to Janossy and Greaves [Clin. Exp. Immunol., 9, 483 (1971) and 10, 535 (1972)]:

"Product cyclosporins" inhibit concanavalin A stimulated DNA-synthesis (inhibition of H$^3$-thymidine incorporation), cell-proliferation and blasto-genesis in mouse-spleen lymphocytes compared with untreated controls at concentrations of from 0.01 to 10 μg/ml.

1.3 Mixed lymphocyte reaction [Bach et al., J. Exp. Med. 136, 1430 (1972)]:

The reaction (i.e. proliferation and differentiation) of lymphocytes [mouse (Balb/c) spleen cells] on co-incubation for 5 days, with allogenic spleen cells from irradiated mice (CBA) is measured in the presence and absence of test-substance serves as control and is taken as 100%. Reaction in the presence of test-substance is expressed as the % change compared with the 100% control reaction. Inhibition of reaction is observed using "Product cyclosporins" at a concentration of from 0.01 to 10 μg/ml$^{-1}$.

2. Anti-inflammatory activity

Anti-inflammatory activity may be shown in the adjuvant arthritis test (established and developing) in the rat. For this test adjuvant arthritis is induced by the method of Pearson and Wood, "Arthr. Rheum." 2, 440 (1959). "Product cyclosporins" are active in this test against developing and established arthritis at doses of from 1 to 30 mg/kg/day p.o.

3. Anti-parasitic activity

Anti-malaria test according to L. Rane, "Chemotherapy and Drug Resistance in Malaria" ed. W. Peters, Academic Press, New York, 1970:

Mice (OF1: male) are infected i.p. on day 0 with 0.2 ml of suspension of erytherocytes containing 10$^7$ cells parisitized by *Plasmodium berghei* (strain NK 65). Test substance is administered p.o. on days 3, 5, 7, 9 and 11 at varying dosages using 5 to 10 mice/dose. The survival time is recorded, and the minimum effective dosage (MED) calculated by comparison of survival time with that for untreated controls. For controls, survival time = ca. 7 days. The MED is the dosage at which survival time is doubled. "Product cyclosporins" are effective in this test at dosages of from 10 to 50 mg/kg/day, p.o.

In addition to the above it is to be noted that "product cyclosporins" are also characterized by reduction of undesirable side-effects, e.g. reduction of toxicity, in particular nephrotoxicity, as compared with hitherto known cyclosporins, for example Cyclosporine, as may be demonstrated in standard animal tests.

In view of their immunosuppressive activity, the said "product cyclosporins" are useful for the prophylaxis and treatment of disease and conditions requiring a reduction of the immune response. Thus they may be used to suppress the proliferation of lymphocytes and immunocytes, e.g. in the treatment of auto-immune diseases or in preventing the rejection of transplants, e.g. skin, bone-marrow and kidney transplants.

Specific auto-immune diseases for which the "product cyclosporins" are useful include all of those for which treatment with Cyclosporine has been proposed or used, for example, aplastic anaemia, pure red cell anaemia, idiopathic thrombocytopaenia, systemic lupus erythematodes, polychondritis, scleroderma, Wegener's granulamatosis, dermatomyositis, chronic active hepatitis, myasthenia gravis, psoriasis, Steven-Johnson syndrome, idiopathic sprue, Crohn's disease, Graves opthalmopathy, sarcoidosis, multiple sclerosis, primary biliary cirrhosis, primary juvenile diabetes, uveitis posterior, interstitial lung fibrosis and psoriatic arthritis.

In view of their immunosuppressive activity and the known immunosuppressive profile of the cyclosporins in relation to suppression of T-cell proliferation, "product cyclosporins" are also indicated for use in the treatment or amelioration of disease caused by leucotropic viruses, in particular human leucotropic retroviruses, for example HTLV-I or III, either alone or in conjunction with other indicated therapy.

In view of their anti-inflammatory activity, the said "product cyclosporins" are also useful for the treatment of inflammatory conditions, in particular inflammatory conditions with an aetiology including an auto-immune component, e.g. for the treatment of arthritis and rheumatic diseases such as poly-arthritis chronica progrediente.

In view of their anti-parasitic activity, the said "product cyclosporins" are also useful for the treatment of parasitic disease, for example schistosomiasis, filariasis, leishmaniasis, coccidioidomycosis and, in particular, malaria.

For the above-mentioned uses the dose will, of course, vary depending on the role of administration, the particular condition to be treated and the therapy desired. In general however, satisfactory results are obtained when administered at a daily dosage of from about 1 to 100, preferably from about 5 to 50, most preferably 10 to 20 mg/kg animal body weight, conveniently administered in divided doses 2 to 3 times a day, or in retard form. For the larger mammals, the total daily dosage is in the range of from about 75 to 5,000, preferably from about 400 to 2,000 and most preferably from about 800 to 1,600 mg and dosage forms suitable for e.g. oral administration comprises from about 15 to 2,500, preferably from about 100 to 2,000, most preferably 200 to 800 mg "product cyclosporin" admixed with a solid or liquid pharmaceutical diluent or carrier.

As noted above a suitable daily dose dosage for any specific "product cyclosporin" will depend in particular on its relative potency of activity. Preferred "product cyclosporins" in accordance with the invention are those of Examples 1 and 23 and, in particular, 21 and 36. For these, obtained results in the above tests are as follows:

| PRODUCT OF EXAMPLE | TEST 1.1 | TEST 1.2 IC$_{50}$ (µg/ml) | TEST 1.3 | TEST 2 ED$_{50}$ mg/kg p.o. | TEST 3 MED mg/kg p.o. |
|---|---|---|---|---|---|
| 1 | 0.06 | <0.04 | 0.026 | 5* 19** | 5 × 15 |
| 21 | 0.085 | | 0.0088 | 5* 13** | 5 × 10 |
| 23 | 0.046 | <0.04 | 0.027 | | 5 × 30 |
| 36 | 0.04 | | 0.085 | <10* 13* | 5 × 15 |

IC$_{50}$ = Concentration giving 50% inhibition compared with untreated controls.
* = result for developing arthritis.
** = result for established arthritis.

In accordance with the foregoing the present invention further provides:

(a) A pharmaceutical composition comprising a "product cyclosporin" together with a pharmaceutically acceptable diluent or carrier therefor;

(b) A "product cyclosporin" for use as a pharmaceutical (i.e. for use in a method of treatment or therapy), in particular for use as an immunosuppresant or anti-inflammatory agent or for use in the treatment of parasitic disease and especially for use in the treatment of any of the specific conditions or diseases hereinbefore set forth; as well as (c) A method of inducing immunosuppression or of treating inflammatory conditions or of treating parasitic disease, in particular of treating any of the specific conditions or diseases hereinbefore set forth, in a subject in need of such treatment, which method comprises administering to said subject an effective amount of a "product cyclosporin".

Compositions as defined under (a) above may be prepared in accordance with techniques known in the art, and include e.g. solutions for oral administration as well as concentrates for administration by infusion.

I claim:

1. A cyclosporin having an optically active, α-N-methylated α-amino acid residue at the 3-position, said residue having the (D)-configuration.

2. A cyclosporin according to claim 1 of formula II

```
┌─X-Y-Z-MeLeu-Val-MeLeu-Ala-(D)Ala-MeLeu-MeLeu-MeVal─┐
  1 2 3   4    5    6    7    8      9    10    11
```
(II)

wherein
X is -MeBmt- or -dihydro-MeBmt-,
Y is -αAbu-, -Thr-, -Val- or -Nva-, and
Z is an optically active, α-N-methylated α-amino acid residue having the (D)-configuration.

3. A cyclosporin according to claim 2, wherein Z has the formula I

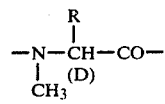

wherein R is:
(i) C$_{1-6}$-alkyl or halo-substituted C$_{1-6}$alkyl;
(ii) hydroxy-(C$_{1-6}$alkyl);
(iii) thio-(C$_{1-6}$alkyl);
(iv) amino-(C$_{1-6}$alkyl);
(v) (C$_{2-5}$alkoxycarbonylamino)-(C$_{1-4}$alkyl);
(vi) nitro-(C$_{1-6}$alkyl) or cyano-(C$_{1-5}$alkyl);
(vii) (C$_{1-6}$alkoxy)-(C$_{1-6}$alkyl) or (C$_{1-6}$alkylthio)-(C$_{1-6}$alkyl);
(viii) (C$_{2-7}$alkanoyloxy)-(C$_{1-6}$alkyl);
(ix) (C$_{2-7}$diazoalkanoyloxy)-(C$_{1-6}$alkyl);
(x) carboxy-(C$_{1-6}$alkyl) or (C$_{2-7}$alkoxycarbonyl)-(C$_{1-6}$alkyl);
(xi) aminocarbonyl-(C$_{1-4}$alkyl);
(xii) aminocarbonyloxy-(C$_{1-4}$alkyl) or amino-(C$_{2-9}$alkanoyloxy)-(C$_{1-4}$alkyl);
(xiii) amino-(C$_{2-9}$alkoxycarbonyl)-(C$_{1-4}$alkyl);
(xiv) C$_{2-7}$-alkylcarbonyl;
(xv) C$_{2-7}$-alkoxycarbonyl;
(xvi) C$_{1-6}$alkylthio or hydroxy-(C$_{1-6}$-alkylthio);
(xvii) (C$_{1-6}$alkoxy)-(C$_{1-6}$alkylthio);
(xviii) (C$_{2-11}$akanoyloxy)-(C$_{2-4}$-alkylthio);
(xix) (C$_{2-11}$alkanoyloxy)-(C$_{2-4}$alkylsulfinyl) or -(C$_{2-4}$-alkylsulfonyl);
(xx) aminocarbonyloxy-(C$_{2-4}$alkylthio) or (C$_{2-11}$aminoalkanoyloxy)-(C$_{2-4}$alkylthio);
(xxi) aminocarbonyloxy-(C$_{2-4}$alkylsulfinyl) or -(C$_{2-4}$alkylsulfonyl), or (C$_{2-11}$aminoalkanoyloxy)-(C$_{2-4}$alkylsulfinyl) or -(C$_{2-4}$alkylsulfonyl);
(xxii) aminocarbonyl;
(xxiii) C$_{3-6}$alkenyl, C$_{3-6}$alkinyl, or halo-substituted C$_{3-6}$alkenyl or C$_{3-6}$alkinyl;
(xxiv) hydroxy-(C$_{3-6}$alkenyl);
(xxv) aryl-(C$_{1-6}$alkyl) or hydroxy-substituted aryl-(C$_{1-6}$alkyl);
(xxvi) aryl-(C$_{3-6}$alkenyl), aryl-(C$_{3-6}$alkinyl), or hydroxy-substituted aryl-(C$_{3-6}$alkenyl) or aryl-(C$_{3-6}$alkinyl);
(xxvii) arylthio;
(xxviii) heteroarylthio;
(xxix) aryl-(C$_{2-5}$alkoxycarbonylamino)-(C$_{1-4}$alkyl);
(xxx) halogen;
(xxxi) cyano; or
(xxxii) a group of formula X—(CH$_2$—CH$_2$—O)$_n$—CH$_2$—CO—O—CH$_2$— wherein n is 1, 2 or 3 and X is amino whereby the multiple bond in groups under (xxiii), (xxiv) and (xxvi) may not be at the β-carbon atom of the completed residue I.

4. A cyclosporin according to claim 3, wherein R is:
(1.a) methyl, ethyl, n-propyl, difluoromethyl, trifluoromethyl or 2,2,2-trifluoroethyl;
(1.b) fluoromethyl;
(ii) hydroxymethyl, 1-hydroxyethyl, 2-hydroxyethyl or 1-hydroxy-n-hexyl;
(iv) aminomethyl, 2-aminoethyl, 3-amino-n-propyl, 4-amino-n-butyl or dimethylaminomethyl;
(vi) 2-nitroethyl or cyanomethyl;
(vii) methoxymethyl or methylthiomethyl;
(viii) acetoxymethyl;
(ix) diazoacetoxymethyl;
(x) carboxymethyl, methoxycarbonylmethyl or t-butoxycarbonyl methyl;
(xi) the group of formula

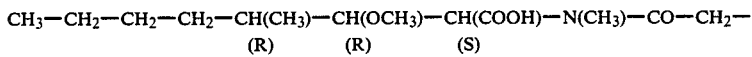

(xv) methoxycarbonyl;
(xvi) methylthio or 2-hydroxy-ethylthio;
(xvii) 2-methoxy-ethylthio;
(xviii) 2-acetoxy-ethylthio;
(xxii) aminocarbonyl or methylaminocarbonyl;
(xxiii.a) allyl, 2-chlorallyl, 3-chloroallyl, 4,4,4-trifluoro-2-butenyl or propargyl;
(xxiii.b) 2-methylallyl or 3,3-dichloroallyl;
(xxiv) 1-hydroxy-6-hexenyl;
(xxv) benzyl, 2-phenethyl, α-hydroxybenzyl or p-hydroxybenzyl;
(xxvii) phenylthio;
(xxviii) 2-pyridylthio;
(xxx.a) iodine;
(xxx.b) fluorine;
(xxxi) cyano; or
(xxxii) a group of formula X—(CH$_2$—CH$_2$—O)-$_n$—CO—O—CH$_2$— wherein n is 2 and X is NH$_2$— or BOC—NH—.

5. A cyclosporin according to claim 3, wherein R has the meanings given under (i) through (iv) inclusive, (vi), (vii), (viii), (x), (xiv) through (xviii) inclusive, (xxii) through (xxv) inclusive, (xxvii) or (xxx).

6. A cyclosporin according to claim 4, wherein R has the meanings given under (1.a), (ii) through (xxii) inclusive, (xxiii.a), (xxiv) through (xxviii), inclusive, (xxx.a), (xxxi) and (xxxii).

7. A cyclosporin according to claim 4, wherein X is -MeBmt-, Y is -Val- and R is CH$_3$—S—.

8. A cyclosporin according to claim 4, wherein X is -dihydro-MeBmt-, Y is -Val- and R is CH$_3$—S—.

9. A cyclosporin according to claim 4, wherein X is -MeBmt-, Y is -αAbu- and R is F.

10. A cyclosporin according to claim 4, wherein X is -MeBmt-, Y is -αAbu- and R is F—CH$_2$—.

11. A cyclosporin according to claim 4, wherein X is -MeBmt-, Y is -αBu- and R is selected from the group consisting of CH$_3$—, CH$_2$=CH—CH$_2$—, CH≡C—CH$_2$—, t.C$_4$H$_9$O—CO—CH$_2$—, CH$_3$—N(CH$_3$)—CH$_2$—, CH$_3$—S—, 2-pyridylthio, phenylthio, CH$_3$O—CO—, HO—CH$_2$—, (L)α-hydroxybenzyl, CH$_3$CO—O—CH$_2$—, HOOC—CH$_2$— and CH$_3$O—CO—CH$_2$—; or X is -MeBMt-, Y is -Nva- and R is selected from the group consisting of CH$_3$—, CH$_2$=CH—CH$_2$—, CH$_3$—S— and CH$_3$O—CO—; or
X is -MeBmt-, Y is -Thr- and R is selected from the group consisting of CH$_3$— and CH$_3$O—CO—; or
X is -MeBmt-, Y is -Val- and R is selected from the group consisting of CH$_3$—, CH$_2$=CH—CH$_2$— and CH$_3$O—CO—; or
X is —dihydro-MeBmt-, Y is -αABu- and R is CH$_2$=CH—CH$_2$—.

12. A cyclosporin according to claim 4, wherein X is -MeBmt-, Y is -αAbu- and R is selected from the group consisting of C$_2$H$_5$—, benzyl, (CIS) Cl—CH=CH—CH$_2$—, (TRANS) Cl—CH=CH—CH$_2$—, Cl—C(Cl)=CH—CH$_2$—, CH$_2$=CCl—CH$_2$—, CH$_2$=C(CH$_3$)—CH$_2$—, —CN, CH$_3$—CH(OH)—, CH$_3$—NH—CO—, HO—(CH$_2$)$_2$—S—, CH$_3$CO—O—(CH$_2$)$_2$—S—, NH$_2$=CH—CO—O—CH$_2$— and t.C$_4$H$_9$O—CO—NH—(CH$_2$)$_2$—O—(CH$_2$)$_2$—O—CH$_2$—CO—O—CH$_2$—; or X is -dihydro-MeBmt-, Y is -Val- and R is selected from the group consisting of CH$_2$=CH—CH$_2$— and nC$_3$H$_7$AA—.

13. A cyclosporin according to claim 1 having the formula II

—X-Y-Z-MeLeu-Val-MeLeu-Ala-(D)Ala-MeLeu-MeLeu-MeVal— (II)
1 2 3   4    5    6    7    8    9    10    11 wherein Z is a group of formula I

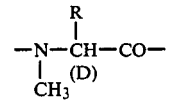

and X is -MeBmt-, Y is -αAbu- and R in formula I is selected from the group consisting of tetrahydropyranyl —O—CH$_2$—CH$_2$—S—, C$_3$H$_7$— and

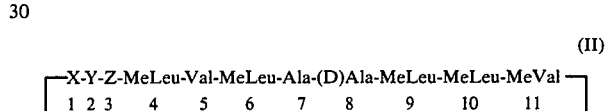

X is -3'-Acetoxy-MeBmt-, Y is -αAbu- and R in formula I is selected from the group consisting of CH$_3$CO—O—CH$_2$—, HO—CH$_2$— and F—CH$_2$—.

14. A pharmaceutical composition comprising a cyclosporin as claimed in claim 1, together with a pharmaceutically acceptable diluent or carrier therefor.

15. A pharmaceutical composition comprising a cyclosporin as claimed in claim 3, together with a pharmaceutically acceptable diluent or carrier therefor.

16. A method of inducing immunosuppression or of treating inflammatory conditions or of treating parasitic disease, in a subject in need of such treatment, which method comprises administering to said subject an effective amount of a cyclosporin as claimed in claim 1.

17. A method of inducing immunosuppression or of treating inflammatory conditions or of treating parasitic disease, in a subject in need of such treatment, which method comprises administering to said subject an effective amount of a cyclosporin as claimed in claim 3.

* * * * *